US 11,452,820 B2

(12) United States Patent
Schabbach et al.

(10) Patent No.: US 11,452,820 B2
(45) Date of Patent: Sep. 27, 2022

(54) MEDICAMENT DELIVERY DEVICE

(71) Applicant: Sanofi-Aventis Deutschland GMBH, Frankfurt am Main (DE)

(72) Inventors: Michael Schabbach, Frankfurt am Main (DE); Beate Franke, Frankfurt am Main (DE); Giuliano Pradel, Besana in Brianza (IT); Ilario Melzi, Milan (IT); Stefan Verlaak, Paderno d'Adda (IT); Andrew Nelson, Dallas, TX (US)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 584 days.

(21) Appl. No.: 16/336,584

(22) PCT Filed: Sep. 20, 2017

(86) PCT No.: PCT/EP2017/073724
§ 371 (c)(1),
(2) Date: Mar. 26, 2019

(87) PCT Pub. No.: WO2018/060026
PCT Pub. Date: Apr. 5, 2018

(65) Prior Publication Data
US 2019/0217017 A1 Jul. 18, 2019

(30) Foreign Application Priority Data
Sep. 27, 2016 (EP) ..................................... 16190884

(51) Int. Cl.
*A61M 5/315* (2006.01)
*A61M 5/32* (2006.01)
(Continued)

(52) U.S. Cl.
CPC .... *A61M 5/31591* (2013.01); *A61M 5/14248* (2013.01); *A61M 5/283* (2013.01);
(Continued)

(58) Field of Classification Search
CPC ............ A61M 5/31591; A61M 5/3158; A61M 5/2033; A61M 2005/14252;
(Continued)

(56) References Cited

U.S. PATENT DOCUMENTS 3,941,130 A * 3/1976 Tibbs .................. A61M 5/2033
604/136
4,886,499 A 12/1989 Cirelli et al.
(Continued)

FOREIGN PATENT DOCUMENTS

| CN | 1723055 | 1/2006 |
| CN | 101001655 | 7/2007 |

(Continued)

OTHER PUBLICATIONS

International Preliminary Report on Patentability in International Application No. PCT/EP2017/073724, dated Apr. 2, 2019, 10 pages.
(Continued)

*Primary Examiner* — Bhisma Mehta
*Assistant Examiner* — John J Crawford
(74) *Attorney, Agent, or Firm* — Fish & Richardson P.C.

(57) ABSTRACT

The present disclosure relates to a medicament delivery device. The medicament delivery device comprises a housing, a needle, a medicament delivery mechanism and an actuator. The actuator is moveable relative to the housing from an initial position to an intermediate position such that the actuator exerts a force on the first locking member to urge the first locking member from a locked state to an unlocked state wherein the first biasing member moves the needle from a retracted position to an extended position. The
(Continued)

actuator is moveable relative to the housing from the intermediate position to a second position such that the actuator exerts a force on the second locking member to urge the second locking member from a locked state to an unlocked state wherein the second biasing member moves the dispensing member within the housing to dispense medicament from the reservoir when the reservoir contains medicament.

26 Claims, 8 Drawing Sheets

(51) Int. Cl.
*A61M 5/142* (2006.01)
*A61M 5/28* (2006.01)
*A61M 5/50* (2006.01)
*A61M 5/145* (2006.01)
*A61M 5/148* (2006.01)

(52) U.S. Cl.
CPC .......... *A61M 5/3234* (2013.01); *A61M 5/502* (2013.01); *A61M 5/148* (2013.01); *A61M 5/1454* (2013.01); *A61M 2005/14256* (2013.01)

(58) Field of Classification Search
CPC .. A61M 2005/14284; A61M 2005/202; A61M 2005/206
See application file for complete search history.

(56) References Cited

U.S. PATENT DOCUMENTS

| | | | | |
|---|---|---|---|---|
| 6,270,479 B1* | 8/2001 | Bergens | ............... | A61M 5/2033 604/156 |
| 2005/0277885 A1 | 12/2005 | Scherer | | |
| 2007/0027430 A1* | 2/2007 | Hommann | .......... | A61M 5/2033 604/207 |
| 2009/0043278 A1 | 2/2009 | Tanaka et al. | | |
| 2010/0010454 A1* | 1/2010 | Marshall | ............. | A61M 5/2033 604/208 |
| 2012/0220954 A1* | 8/2012 | Cowe | ................. | A61M 5/2033 604/228 |
| 2013/0110049 A1 | 5/2013 | Cronenberg et al. | | |
| 2013/0338592 A1* | 12/2013 | Calasso | ............. | A61M 5/14232 604/151 |
| 2015/0011976 A1* | 1/2015 | Vouillamoz | ........... | A61M 5/172 604/507 |
| 2017/0224915 A1* | 8/2017 | Destefano | ............. | A61M 5/142 |

FOREIGN PATENT DOCUMENTS

| | | |
|---|---|---|
| CN | 101184523 | 5/2008 |
| CN | 101616709 | 12/2009 |
| CN | 103476445 | 12/2013 |
| CN | 103857427 | 6/2014 |
| CN | 104245022 | 12/2014 |
| CN | 105492042 | 4/2016 |
| EP | 1884259 | 2/2008 |
| EP | 2674177 | 12/2013 |
| JP | H03-501348 | 3/1991 |
| JP | H06-504215 | 5/1994 |
| JP | 2008-512193 | 4/2008 |
| JP | 2013-526366 | 6/2013 |
| JP | 2015-511528 | 4/2015 |
| WO | WO 1989/012473 | 12/1989 |
| WO | WO 1992/011879 | 7/1992 |
| WO | WO 2004/030728 | 4/2004 |
| WO | WO 2005/115512 | 12/2005 |
| WO | WO 2006/031500 | 3/2006 |
| WO | WO 2008/101892 | 8/2008 |
| WO | WO 2011/146166 | 11/2011 |
| WO | WO 2012/110573 | 8/2012 |
| WO | WO 2013/016376 | 1/2013 |
| WO | WO 2013/114221 | 8/2013 |
| WO | WO 2015/011488 | 1/2015 |
| WO | WO 2016/053954 | 4/2016 |

OTHER PUBLICATIONS

International Search Report and Written Opinion in International Application No. PCT/EP2017/073724, dated Dec. 11, 2017, 14 pages.

* cited by examiner

MEDICAMENT DELIVERY DEVICE

CROSS REFERENCE TO RELATED APPLICATIONS

The present application is the national stage entry of International Patent Application No. PCT/EP2017/073724, filed on Sep. 20, 2017, and claims priority to Application No. EP 16190884.3, filed on Sep. 27, 2016, the disclosures of which are incorporated herein by reference.

TECHNICAL FIELD

The present disclosure relates to a medicament delivery device.

BACKGROUND

A variety of diseases exist that require regular treatment by injection of a medicament and such injections can be performed by using injection devices. Various injection devices for delivering injections of medicament are known in the art. Another type of injection pump that is gaining traction is the bolus injector device. Some bolus injector devices are intended to be used with relatively large volumes of medicament, typically at least 1 ml and maybe a few ml. Injection of such large volumes of medicament can take some minutes or even hours. Such high capacity bolus injector devices can be called large volume devices (LVDs). Generally such devices are operated by the patients themselves, although they may also be operated by medical personnel.

SUMMARY

In some aspects, an improved medicament delivery device is provided.

In one aspect, there is provided a medicament delivery device comprising: a housing; a needle moveable from a retracted position, wherein the needle is fully received in the housing, to an extended position, wherein the needle protrudes out of the housing; a medicament delivery mechanism comprising a reservoir and dispensing member each disposed in the housing, first and second biasing members, and first and second locking members; and, an actuator moveable relative to the housing from an initial position to an intermediate position such that the actuator exerts a force on the first locking member to urge the first locking member from a locked state to an unlocked state wherein the first biasing member moves the needle from the retracted position to the extended position, wherein the actuator is moveable relative to the housing from the intermediate position to a second position such that the actuator exerts a force on the second locking member to urge the second locking member from a locked state to an unlocked state wherein the second biasing member moves the dispensing member within the housing to dispense medicament from the reservoir when the reservoir contains medicament.

Advantageously, the medicament delivery device utilises the same actuator to initiate movement of the needle to the extended position and dispense medicament from the reservoir. This makes the medicament delivery device compact and easy to use. The patient may move the actuator from the first position to the second position, via the intermediate position, in one motion to move the needle to the extended position and dispense medicament from the reservoir.

In one embodiment, the actuator comprises a push button that is slidable relative to the housing.

In one embodiment, the actuator comprises a slide member that is slid relative to the housing. In one such embodiment, the actuator is mounted on a rail and is slidable along the rail to move relative to the housing between the first position, intermediate position and second positon. In one embodiment, the housing comprises a slot and the slide member extends out of the slot. The user is able to slide the slide member within the slot from the initial position to the intermediate position and from the intermediate position to the second position.

In another embodiment, the actuator is rotatable relative to the housing to move from the initial position to the intermediate position and from the intermediate position to the second position. In one such embodiment, the actuator comprises a screw thread that engages with a screw thread of the housing. Thus, rotation of the actuator relative to the housing results in linear movement of the actuator relative to the housing. In one such embodiment, when the actuator is in the first position, rotation of the actuator relative to the housing causes the screw threads to engage such that the actuator moves linearly to the intermediate position, and when the actuator is in the intermediate position, rotation of the actuator relative to the housing causes the screw threads to engage such that the actuator moves linearly to the second position. In one such embodiment, the housing comprises a recess having a radially-inwardly facing screw thread and the actuator comprises a member with a radially-outwardly facing screw thread that engages the screw thread of the recess. In one such embodiment, the actuator is screwed in to the recess upon rotation by the user to move from the first position to the second position.

The first and/or second locking member may be pivotally coupled to the housing.

In one embodiment, the first locking member comprises a projection and the actuator is configured to abut the projection when the actuator is moved from the first position to the intermediate position to move the first locking member to the unlocked state. The first locking member may comprise a surface configured to resist movement of the needle to the extended position when the first locking member is in the locked state, wherein the first locking member is pivotally coupled to the housing at a point between the surface and the projection. Therefore, accidental movement of the needle to the extended position is prevented.

In one embodiment, the second locking member comprises a first portion and a second portion extending at an angle to the first portion, wherein the first portion abuts the dispensing member when the second locking member is in the locked state. The first portion may comprise a recess configured to receive at least part of the dispensing member when the second locking member is in the locked state. The actuator may be configured to abut the second portion when the actuator is moved from the intermediate position to the second position to move the second locking member to the unlocked state.

In one embodiment, the medicament delivery mechanism further comprises a third biasing member and a third locking member, wherein the third locking member is moveable from a locked state to an unlocked state wherein the third biasing member moves the needle to the retracted position. The second biasing member may be configured to urge the dispensing member against the third locking member such that the third locking member is moved to the unlocked state. Thus, the needle may be automatically moved back to the retracted position once medicament has been dispensed from the reservoir and safely stored in the housing.

In one embodiment, the third locking member is pivotally coupled to the housing and comprises a first portion and a second portion extending at an angle to the first portion, wherein the second biasing member is configured to urge the dispensing member against the first portion of the third locking member.

The second portion of the third locking member may comprise a projection configured to retain the second biasing member in a compressed state when the third locking member is in the locked state.

In one embodiment, the housing comprises a distal end wall with an adhesive layer. Therefore, the housing may be attached to an injection site of the patient.

In one embodiment, the first locking member prevents the first biasing member from moving the needle from the retracted position to the extended position when the first locking member is in the locked state.

In one embodiment, the second locking member prevents the second biasing member from moving the dispensing member within the housing when the second locking member is in the locked state.

The housing may comprise first and second portions that are moveable relative to each other from an initial position to a primed position. In one embodiment, movement of the first and second portions from the initial position to the primed position primes the first biasing member. In one embodiment, movement of the first and second portions from the initial position to the primed position primes the second biasing member. In one embodiment, movement of the first and second portions from the initial position to the primed position primes the first biasing member and the second biasing member. In one embodiment, the first and second portions are slid relative to each other to move from the initial position to the primed position. In another embodiment, the first and second portions are rotated relative to each other to move from the initial position to the primed position. In one such embodiment, the first and second portions comprise screw threads that engage.

The reservoir may contain a medicament.

In one embodiment, the medicament delivery device comprises a large volume device.

In another aspect, there is also provided a method of dispensing medicament from a medicament delivery device that has a housing, a needle, an actuator and a medicament delivery mechanism with a reservoir, a dispensing member, first and second biasing members and first and second locking members, the method comprising: moving the actuator relative to the housing from an initial position to an intermediate position such that the actuator exerts a force on the first locking member to urge the first locking member from a locked state to an unlocked state wherein the first biasing member moves the needle from a retracted position, wherein the needle is fully received in the housing, to an extended position, wherein the needle protrudes out of the housing; and, moving the actuator relative to the housing from the intermediate position to a second position such that the actuator exerts a force on the second locking member to urge the second locking member from a locked state to an unlocked state wherein the second biasing member moves the dispensing member within the housing to dispense medicament from the reservoir.

These and other aspects of the invention will be apparent from and elucidated with reference to the embodiments described hereinafter.

BRIEF DESCRIPTION OF THE FIGURES

Embodiments of the invention will now be described, by way of example only, with reference to the accompanying drawings, in which.

DETAILED DESCRIPTION

Figure 1:
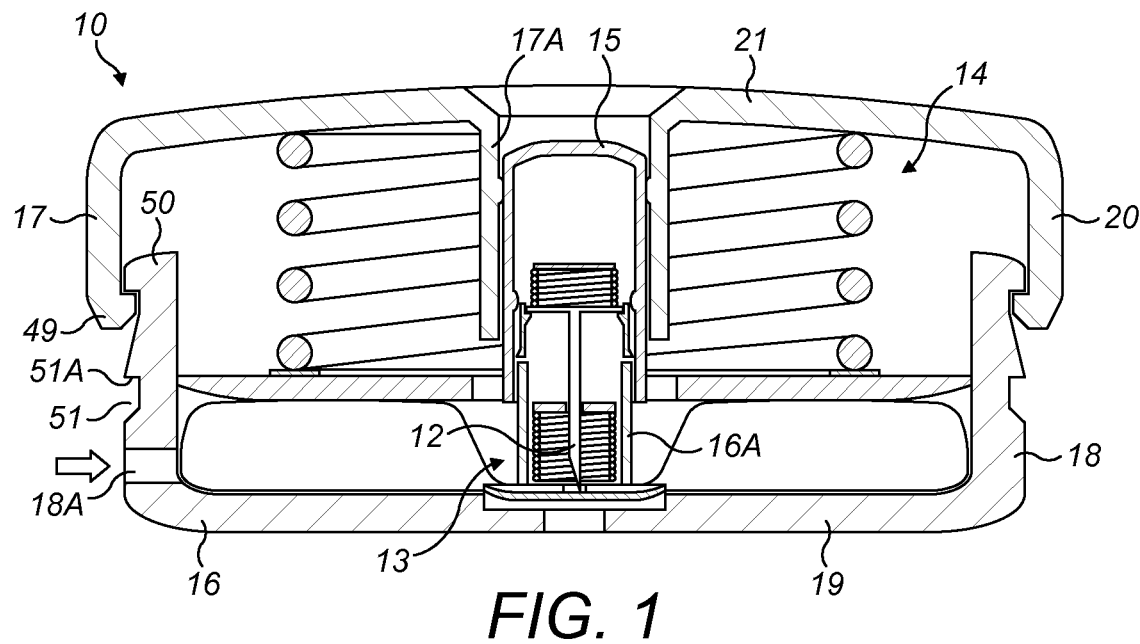
FIG. 1 is a schematic cross-sectional side view of a medicament delivery device according to a first embodiment of the invention, wherein a proximal portion of the housing is in an initial position.

A medicament delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for a large volume device). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

FIGS. 1 to 9B show a medicament delivery device 10, which in the exemplary embodiment comprises a bolus injector device, according to a first embodiment of the invention. The medicament delivery device 10 may be in the form of a large volume device.

The medicament delivery device 10 comprises a housing 11, a needle 12, a needle actuating mechanism 13, a dispensing mechanism 14 and an actuator 15.

The housing 11 comprises a distal portion 16 and a proximal portion 17. The term "distal" refers to a location that is relatively closer to a site of injection and the term "proximal" refers to a location that is relatively further away from the injection site.

The distal portion 16 of the housing 11 comprises a cylindrical peripheral wall 18 and an end wall 19 that together have a generally U-shaped cross-section. The distal portion 16 of the housing 11 further comprises a cylindrical internal wall 16A that is arranged concentrically with the cylindrical peripheral wall 18 of the distal portion 16. The proximal portion 17 of the housing 11 comprises a cylindrical peripheral wall 20 and an end wall 21 that together have a generally U-shaped cross-section. The proximal portion 17 of the housing 11 comprises a cylindrical internal wall 17A that is arranged concentrically with the cylindrical peripheral wall 20 of the proximal portion 17.

The peripheral wall 18 of the distal portion 16 of the housing 11 is slidably received in the peripheral wall 20 of the proximal portion 17 such that the end wall 19 of the distal portion 16 is spaced from the end wall 21 of the proximal portion 17 and a recess 22 is formed therebetween. The distal and proximal portions 16, 17 of the housing 11 together form a generally cylindrical shape that has a central axis (see the dashed line A-A in FIG. 2).

The end wall 19 of the distal portion 16 has an outer surface 19A and an inner surface 19B and the end wall 21 of the proximal portion 17 has an outer surface 21A and an inner surface 21B. One or both of the outer surfaces 19A, 21A of the end walls 19, 21 of the distal and proximal portions 16, 17 may be substantially flat.

The outer surface 19A of the end wall 19 of the distal portion 16 comprises an adhesive layer (not shown) that is initially covered by a label (not shown). In use, the label is removed from the adhesive layer and then the adhesive layer is stuck to the patient's skin at the injection site of the patient such that the end wall 19 of the distal portion 16 is adhered to the injection site.

The dispensing mechanism 14 comprises a medicament reservoir 23, a dispensing member 24, a dispensing biasing member 25 and a dispensing lock 26.

The medicament reservoir 23 is in the form of an annular flexible bag 23. The flexible bag 23 is disposed in the recess 22 in the housing 11 and abuts the inner surface 19B of the end wall 19 of the distal portion 16. The flexible bag 23 is fluidly connected to an aperture 18A in the peripheral wall 18 of the distal portion 16. The aperture 18A forms a filling port 18A that allows for the flexible bag 23 to be filled with medicament through the peripheral wall 18 of the distal portion 16. The flexible bag 23 and/or the aperture 18A may comprise a one-way valve (not shown) that is configured to prevent medicament from flowing out of the flexible bag 23 via the aperture 18A. Alternatively, or additionally, a bung (not shown) may be provided that is inserted into the aperture 18A to seal the aperture 18A after the flexible bag 23 has been filled with medicament.

The dispensing member 24 is in the form of a plate 24. The plate 24 may be annular. The plate 24 is disposed in the recess 22 in the housing 11 such that the flexible bag 23 is located between a distal-facing surface 24A of the plate 24 and the inner surface 19B of the end wall 19 of the distal portion 16. The plate 24 is slidable in the recess 22 in the direction of the central axis A-A of the housing 11 such that the plate 24 is moveable relative to flexible bag 23.

The dispensing biasing member 25 is in the form of a dispensing spring 25. The dispensing spring 25 may be a helical spring. The dispensing spring 25 is disposed in the recess 22 in the housing 11 and extends about the central axis A-A of the housing 11. The dispensing spring 25 is positioned between the internal wall 17A of the proximal portion 17 and the peripheral wall 20 of the proximal portion 17.

The dispensing spring 25 is disposed on the opposite side of the plate 24 to the flexible bag 23. A first end of the dispensing spring 25 is located against the inner surface 21B of the end wall 21 of the proximal portion 17 and a remote second end of the dispensing spring 25 is located against a proximal-facing surface 24B of the plate 24.

The proximal portion 17 is moveable relative to the distal portion 16 of the housing 11 between an initial position (shown in FIG. 1) and a primed position (shown in FIGS. 2, 4, 7 and 8). When the proximal portion 17 is in the initial position, the end wall 21 of the proximal portion 17 is spaced from the plate 24 and the end wall 19 of the distal portion 16 such that the dispensing spring 25 is substantially uncompressed. Furthermore, when the proximal portion 17 is in the initial position, only a small section of the peripheral wall 18 of the distal portion 16 is received in the peripheral wall 20 of the proximal portion 17.

When the proximal portion 17 is moved to the primed position, the end wall 21 of the proximal portion 17 is moved towards the end wall 19 of the distal portion 16 such that the distance between the end walls 19, 21 is reduced. An increased amount of the peripheral wall 18 of the distal portion 16 is received in the peripheral wall 20 of the proximal portion 17 when the proximal portion 17 is in the primed position.

The dispensing lock 26 comprises a pair of dispensing locking members 27 that are connected to the distal portion 16 of the housing 11 by corresponding pivotal couplings 28. Each of the dispensing locking members 27 comprises an elongate member 29 and a projection 30 that is integrally formed with the elongate member 29.

The elongate members 29 have a first end 29A and a second end 29B. The elongate members 29 are each attached to a corresponding pivotal coupling 28 towards the first end 29A of the elongate members 29. The second end 29B of each elongate member 29 is spaced from the corresponding pivotal coupling 28 such that each second end 29B is pivotable about the corresponding pivotal coupling 28. A recess 29C is provided in the second end 29B of each elongate member 29.

The projection 30 of each dispensing locking member 27 extends at an angle from a corresponding elongate member 29 and is located proximate to the first end 29A of the elongate member 29. Each projection 30 has a free end 30A that is remote to said corresponding elongate member 29. The elongate member 29 and projection 30 may be arranged such that the dispensing locking members 27 are each generally L-shaped or V-shaped.

Figure 4:
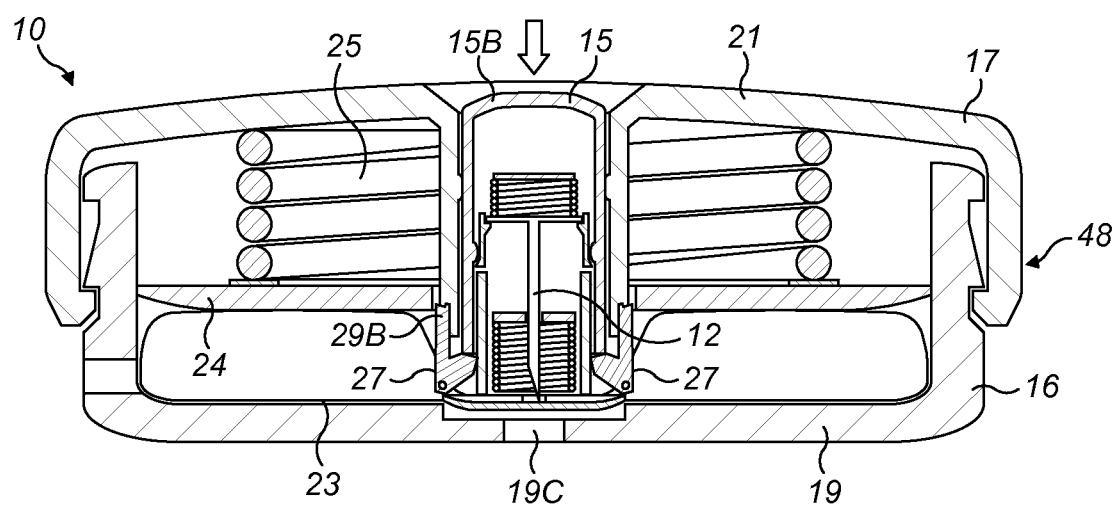
FIG. 4 is a schematic cross-sectional side view of the medicament delivery device of FIG. 1, wherein the button is partially depressed into the housing and a needle is in a retracted position.
Figure 6:
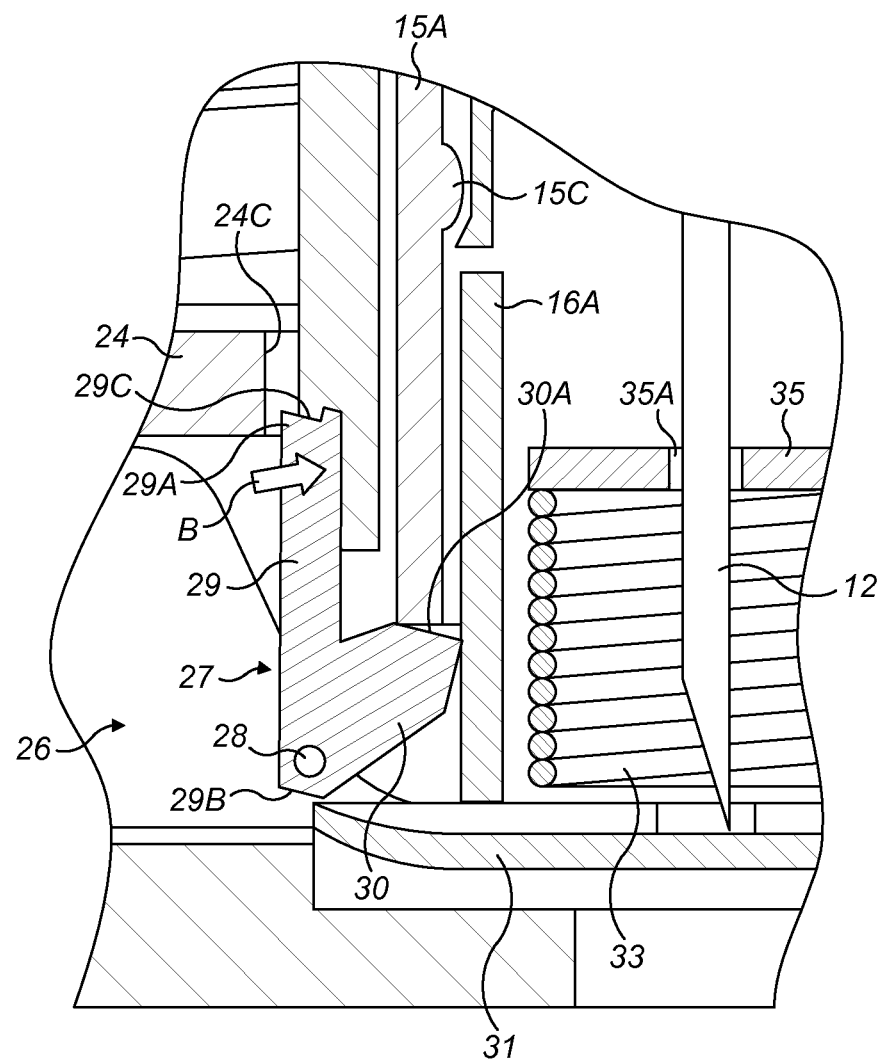
FIG. 6 is a close-up schematic cross-sectional side view of a dispensing lock of the medicament delivery device of FIG. 1, wherein a pair of extension locking members are moved to an unlocked state.

The dispensing locking members 27 are pivotable from a locked state (shown in FIGS. 2 and 3) to an unlocked state (shown in FIGS. 4 and 6). In the locked state, each of the dispensing locking members 27 is positioned such that the elongate member 29 extends towards the end wall 21 of the proximal portion 17 at an angle away from the central axis A-A of the housing 11 in the direction from the first end 29A to the second end 29B of the elongate member 29. Moreover, in the locked state, the dispensing locking members 27 are positioned such that the projections 30 extend towards the end wall 21 of the proximal portion 17 at an angle towards the central axis A-A of the housing 11 in the direction towards the free end 30A of the projection 30.

When the dispensing locking members 27 are in the locked state, the plate 24 is located in the recesses 29C of the elongate members 29 such that the plate 24 is prevented from moving towards the end wall 19 of the distal portion 16 of the housing 11. The configuration of the recesses 29C is such that a portion of each elongate member 29 abuts a radially inwardly facing surface 24C of the plate 24 and therefore, when the dispensing locking members 27 are in the locked state and abut the plate 24, the dispensing locking members 27 are prevented from rotating in a direction wherein the second ends 29B of the elongate members 29 move radially outwardly away from the central axis A-A of the housing 11.

The dispensing locking members 27 are moveable to the unlocked state, wherein the dispensing locking members 27 are rotated (in the direction of arrow 'B' in FIG. 6) such that the second end 29B of each elongate member 29 and the free end 30A of the corresponding projection 30 pivot about the respective pivotal couplings 28 to move radially inwardly towards the central axis A-A of the housing 11. When the dispensing locking members 27 are in the unlocked state, the second end 29B of each elongate member 29 is spaced from the plate 24 such that the plate 24 is not received in the recesses 29C of the elongate members 29. Therefore, the plate 24 is not restricted from moving towards the end wall 19 of the distal portion 16 by the dispensing locking members 27.

The actuator 15 is in the form of a button 15 that has a peripheral wall 15A and an end wall 15B. The button 15 is received in the proximal portion 17 of the housing 11 such that the peripheral wall 15A of the button 15 is located on the inside of the internal wall 17A of the proximal portion 17 and is concentrically aligned therewith. The button 15 is slidable within the internal wall 17A of the proximal portion 17 in the direction of the central axis A-A of the housing 11.

Figure 7:
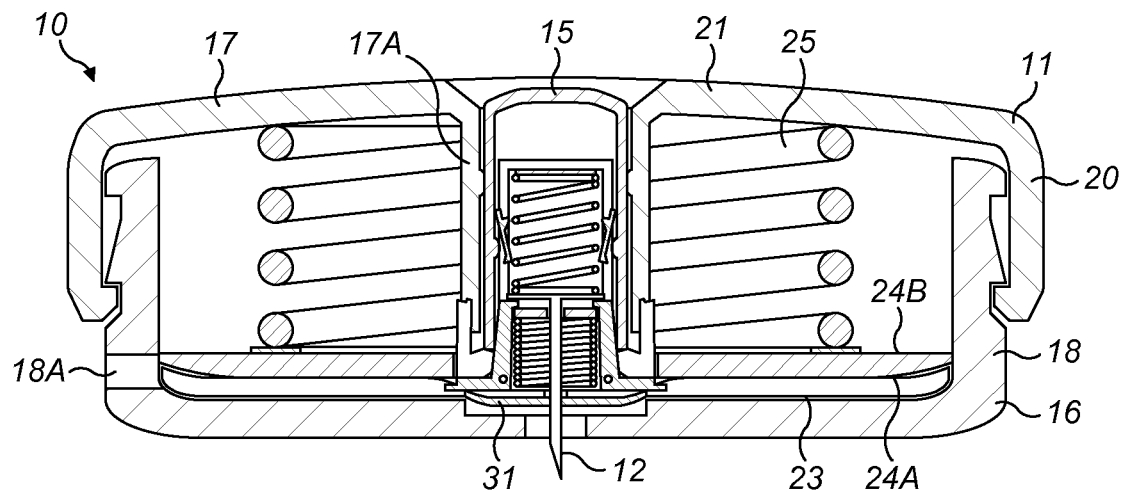
FIG. 7 is a schematic cross-sectional side view of the medicament delivery device of FIG. 1, wherein the needle is in an extended position and medicament is dispensed from the needle.
Figure 8:
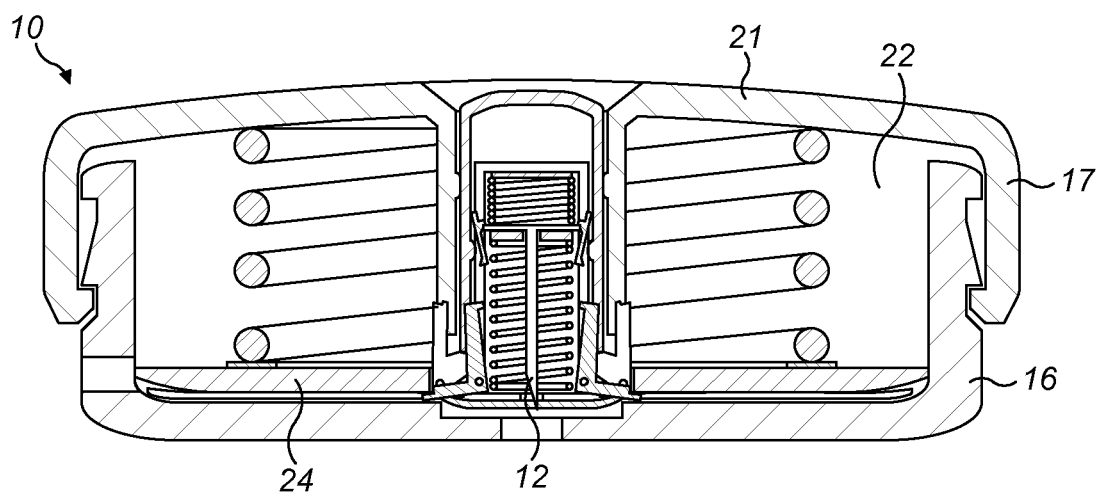
FIG. 8 is a schematic cross-sectional side view of the medicament delivery device of FIG. 1, wherein the needle is in the retracted position.
Figure 9A:
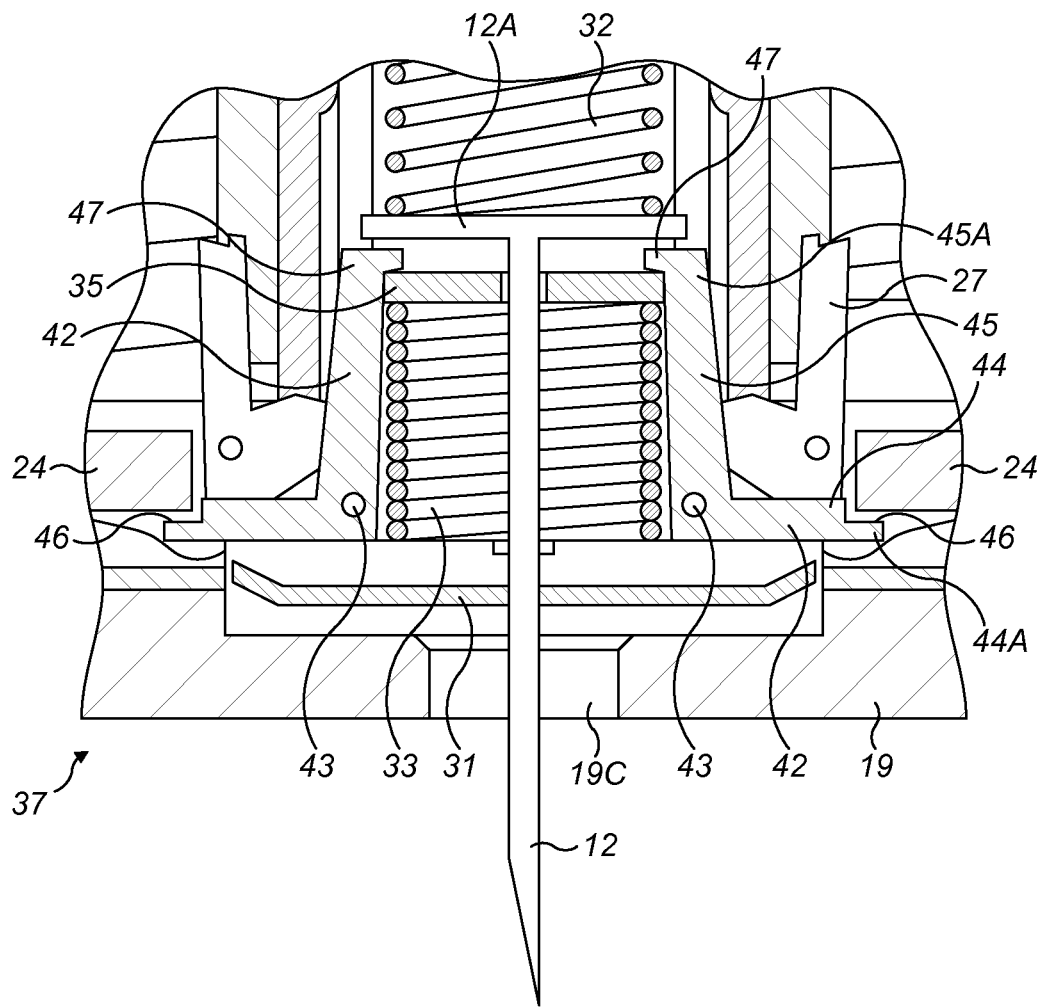
FIG. 9A is a close-up schematic cross-sectional side view of a needle retraction lock of the medicament delivery device of FIG. 1, wherein a pair of retraction locking members are in a locked state; and, FIG. 9B is a close-up schematic cross-sectional side view of the needle retraction lock of the medicament delivery device of FIG. 1, wherein the pair of retraction locking members are in an unlocked state.

The needle 12 is moveable relative to the distal portion 16 of the housing 11 between a retracted position (shown in FIGS. 1 to 4, 8 and 9B) and an extended position (shown in FIGS. 7 and 9A). When the needle 12 is in the retracted position, the needle 12 is fully received in the recess 22 in the housing 11 such that the needle 12 is shielded to prevent damage to the needle 12 and to protect the patient from being accidentally injured by the needle 12.

When the needle 12 is moved from the retracted position to the extended position, the needle 12 is moved linearly in the direction of the central axis A-A of the housing 11 such that the end of the needle 12 projects out of an aperture 19C in the end wall 19 of the distal portion 16. Thus, when the adhesive layer of the distal portion 16 is adhered to the injection site of a patient, the needle 12 pierces the patient's skin to extend into the injection site to deliver medicament thereto.

The medicament delivery device 10 further comprises a septum 31 that is fixed to the inner surface 19B of the end wall 19 of the distal portion 16. The septum 31 is located over the aperture 19C in the end wall 19 of the distal portion 16. The needle 12, which is initially in the retracted position, is protected by the septum 31. More specifically, the septum 31 prevents the ingress of contaminants through the aperture 19C in the end wall 19 of the distal portion 16 and into contact with the sterile needle 12. When the needle 12 is moved to the extended position, the needle 12 pierces the septum 31 and the end of the needle 12 passes through the septum 31 to project from the end wall 19. The septum 31 may be manufactured from an impermeable material such as plastic, rubber or metal foil. In alternative embodiments, the septum 31 is fixed to the outer surface 19A of the end wall 19 of the distal portion 16 or is located in the aperture 19C in the end wall 19.

The needle actuating mechanism 13 comprises needle extension and retraction biasing members 32, 33, extension and retraction holding elements 34, 35, and needle extension and retraction locks 36, 37.

The needle extension biasing member 32 is in the form of a needle extension spring 32. The needle extension spring 32 may be a helical spring. The needle extension spring 32 is located inside the peripheral wall 15A of the button 15 and extends about the central axis A-A of the housing 11. The needle extension spring 32 is disposed between a base 12A of the needle 12 and the extension holding element 34.

The extension holding element 34 is fixed relative to the distal portion 16 of the housing 11 and is located on the opposite side of the base 12A of the needle 12 to the septum 31. The extension holding element 34 is configured to act as a stop against which the proximal end of the needle extension spring 32 abuts such that the proximal end of the needle extension spring 32 is prevented from moving towards the end wall 21 of the proximal portion 17 in the direction of the central axis A-A of the housing 11. When the needle 12 is in the initial retracted position, the needle extension spring 32 is compressed between the base 12A of the needle 12 and the extension holding element 34 such that the needle extension spring 32 urges the needle 12 away from the extension holding element 34 in the direction of the central axis A-A of the housing 11 such that the needle 12 is biased to move into the extended position.

The needle extension lock 36 comprises a pair of extension locking members 38 that are connected to the distal portion 16 of the housing 11 by respective pivotal couplings 39. Each of the extension locking members 38 comprises an elongate member 38A and first and second projections 40, 41 that are integrally formed with the elongate member 38A. The first projection 40 is located at the distal end of the elongate member 38A and the second projection 41 is located towards the proximal end of the elongate member 38A.

Each elongate member 38A is attached to the respective pivotal coupling 39 at a point between the proximal and distal ends of the elongate member 38A such that the first and second projections 40, 41 are pivotable about the respective pivotal coupling 39.

Figure 5:
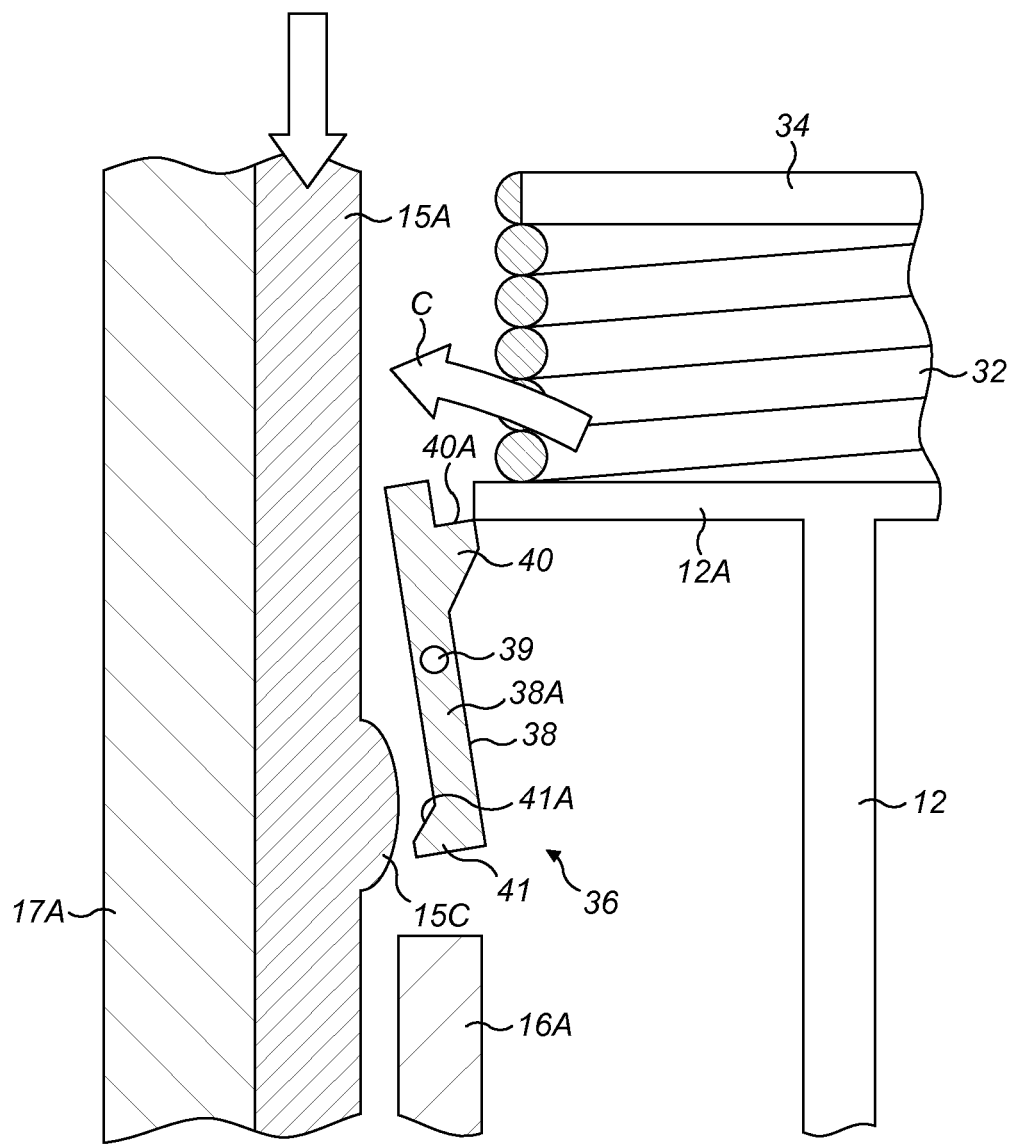
FIG. 5 is a close-up schematic cross-sectional side view of a needle extension lock of the medicament delivery device of FIG. 1, wherein a pair of needle locking members are moved to an unlocked state.

The extension locking members 38 are moveable from a locked state (shown in FIG. 3) to an unlocked state (shown in FIG. 5). In the locked state, the extension locking members 38 are positioned such that the elongate members 38A extend substantially parallel to the central axis A-A of the housing 11 and the first projection 40 of each extension locking member 38 is located nearer to the end wall 21 of the proximal portion 17 of the housing 11 than the second projection 41.

The first projection 40 of each extension locking member 38 extends radially inwardly towards the central axis A-A of the housing 11 when the extension locking members 38 are in the locked state. Each of the first projections 40 comprises a proximal-facing surface 40A that abuts the base 12A of the needle 12 when the extension locking members 38 are in the locked state such that movement of the needle 12 in the direction of the central axis A-A of the housing 11 towards the end wall 19 of the distal portion 16 is prevented. Thus, when the extension locking members 38 are in the locked state, the extension locking members 38 retain the needle 12 in the retracted position against the force of the needle extension spring 32, which is held in a compressed state between the base 12A of the needle 12 and the extension holding element 34.

The second projection 41 of each extension locking member 38 extends radially outwardly away from the central axis A-A of the housing 11 when the extension locking members 38 are in the locked state. Each of the second projections 41 comprises an angled surface 41A that faces at an angle away from the central axis A-A of the housing 11 and towards the end wall 21 of the proximal portion 17.

The button 15 comprises a lip 15C that extends radially inwardly from the inside of the peripheral wall 15A of the button 15 in the direction towards the central axis A-A of the housing 11. The lip 15C may be generally annular.

The lip 15C of the button 15 is configured to abut the angled surface 41A of both of the extension locking members 38 when the button 15 is moved within the housing 11 towards the end wall 19 of the distal portion 16. This causes the second projection 41 of each extension locking member 38 to be urged radially inwardly towards the central axis A-A such that the extension locking members 38 are rotated from the locked state to the unlocked state (in the direction of arrow 'C' in FIG. 5). In the unlocked state, the first projections 40 are moved radially outwardly such that they no longer abut the base 12A of the needle 12 and therefore the base 12A of the needle 12 is able to move away from the extension holding element 34 under the force of the needle extension spring 32. Thus, when the extension locking members 38 are in the unlocked state, the needle 12 moves from the retracted position to the extended position under the force of the needle extension spring 32.

The needle retraction biasing member 33 is in the form of a needle retraction spring 33. The needle retraction spring 33 may be a helical spring. The needle retraction spring 33 is located inside the distal portion 16 of the housing 11 and extends about the central axis A-A thereof. The needle retraction spring 33 is disposed between the retraction holding element 35 and the septum 31. The septum 31 is fixed relative to the distal portion 16 of the housing 11 and therefore acts as a stop against which the distal end of the needle retraction spring 33 abuts.

The retraction holding element 35 is slidably received in the internal wall 16A of the distal portion 16 of the housing 11. The needle retraction spring 33 is initially compressed between the septum 31 and the retraction holding element 35 such that the needle retraction spring 33 urges the retraction holding element 35 away from the septum 31 in the direction of the central axis A-A of the housing 11. The needle retraction lock 37 initially retains the retraction holding element 35 in position against the force of the needle retraction spring 33 such that the needle retraction spring 33 is compressed.

The needle retraction lock 37 comprises a pair of retraction locking members 42 that are connected to the distal portion 16 of the housing 11 by respective pivotal couplings 43. Each of the retraction locking members 42 comprises first and second elongate members 44, 45, a recess 46, and a projection 47. The first and second elongate members 44, 45 are integrally formed at one end. The first and second elongate members 44, 45 extend at an angle to each other. In the present embodiment, the first and second elongate members 44, 45 of each retraction locking member 42 extend substantially perpendicular to each other.

The first and second elongate members 44, 45 comprise respective free ends 44A, 45B that are remote to the pivotal coupling 43. The recess 46 is located at the free end 44A of the first elongate member 44 and the projection 47 is located at the free end 45A of the second elongate member 45.

Figure 9B:
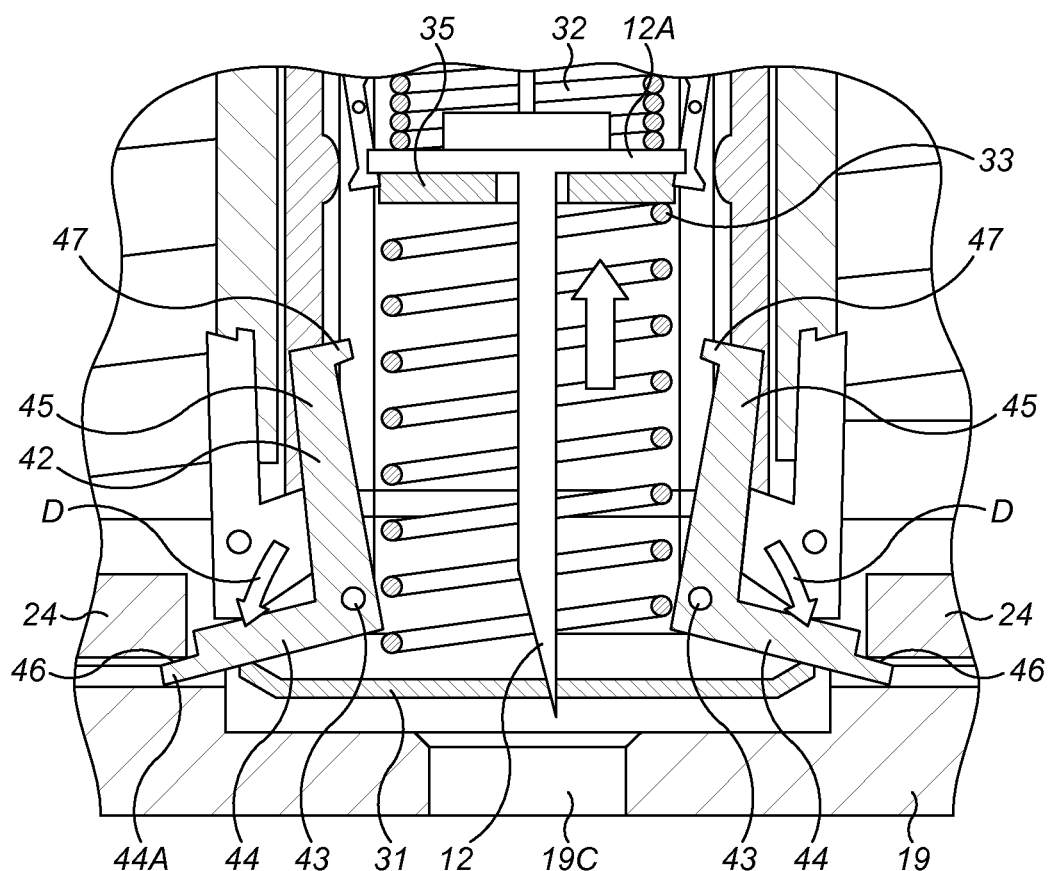

The retraction locking members 42 are pivotable from a locked state (shown in FIG. 9A) to an unlocked state (shown in FIG. 9B). In the locked state, each of the retraction locking members 42 is positioned such that the first elongate members 44 extend radially outwardly away from the central axis A-A of the housing 11 and, in one embodiment, are substantially perpendicular to the central axis A-A of the housing 11. The free end 44A of each first elongate member 44 overlaps the plate 24 in the radial direction. Moreover, in the locked state, each of the retraction locking members 42 is positioned such that the second elongate members 45 extend towards the end wall 21 of the proximal portion 17 from the respective pivotal coupling 43 and, in one embodiment, are substantially parallel to the central axis A-A of the housing 11.

When the retraction locking members 42 are in the locked state, the projection 47 of each retraction locking member 42 extends radially inwardly towards the central axis A-A of the housing 11 to abut a proximal-facing surface of the retraction holding element 35. Thus, the retraction holding element 35 is prevented from moving towards the end wall 21 of the proximal portion 17 and thus the needle retraction spring 33 is held in a compressed state between the septum 31 and the retraction holding element 35.

Movement of the plate 24 within the housing 11 towards the end wall 19 of the distal portion 16, due to operation of the dispensing mechanism 14, causes the plate 24 to be urged against the free end 44A of each first elongate member 44 such that the plate 24 is received in the recess 46 of each first elongate member 44. Thus, the movement of the plate 24 towards the end wall 19 of the distal portion 16 results in a force being exerted on the free end 44A of each first elongate member 44. This force causes the free end 44A of each first elongate member 44 to be urged towards the end wall 19 of the distal portion 16 such that each retraction locking member 42 is urged to rotate about a respective pivotal coupling 43 from the locked state to the unlocked state (in the direction of arrow D' in FIG. 9B).

When the retraction locking members 42 are rotated to the unlocked state, the projection 47 at the free end 45A of each second elongate member 45 is moved radially outwardly away from the central axis A-A of the housing 11 such that the projections 47 are spaced from the retraction holding element 35. Thus, the projections 47 no longer hold the retraction holding element 35 in place against the force of the needle retraction spring 33 and so the retraction holding element 35 is moved towards the end wall 21 of the proximal end 17 by the needle retraction spring 33.

The needle 12 extends through an aperture 35A in the retraction holding element 35 such that when the needle 12 is in the extended position and the retraction locking members 42 are in the locked state (as shown in FIG. 9A) the base 12A of the needle 12 is located in proximity to the retraction holding element 35. Thus, when the retraction locking members 42 are subsequently moved to the unlocked state, the retraction holding element 35 is released such that the needle retraction spring 33 urges the retraction holding element 35 against the base 12A of the needle 12 to move the needle 12 towards the end wall 21 of the proximal portion 17 and into the retracted position (as shown in FIG. 9B).

A clearance gap (not shown) may be provided between each retraction locking member 42 and the septum 31 and end wall 19 of the distal portion 16 to facilitate movement of the retraction locking members 42 between the locked and unlocked states. Alternatively, the septum 31 may be manufactured from a flexible material that facilitates movement of the retraction locking members 42.

The medicament delivery device 10 further comprises a coupling 48 between the distal and proximal portions 16, 17 of the housing 11. The coupling 48 is configured to resist the proximal portion 17 from being moving away from the primed position towards the initial position. The coupling 48 may be configured to prevent the force of the dispensing spring 25, which is located between the plate 24 and the end wall 21 of the proximal portion 17, from moving the end wall 21 of the proximal portion 17 away from the end wall 19 of the distal portion 16 when the proximal portion 17 is in the primed position.

The coupling 48 is in the form of a latch 48. The latch 48 comprises first, second and third stops 49, 50, 51. The first stop 49 is in the form of a first lip 49 that is integrally formed with the peripheral wall 20 of the proximal portion 17 of the housing 11. The first lip 49 extends radially inwardly towards the central axis A-A of the housing 11. The first lip 49 extends from the end of the peripheral wall 20 of the proximal portion 17 that is remote to the end wall 21 of the proximal portion 17. The first lip 49 comprises a proximal-facing surface 49A.

The second stop 50 is in the form of a second lip 50 that is integrally formed with the peripheral wall 18 of the distal portion 16. The second lip 50 extends radially outwardly away from the central axis A-A of the housing 11. The second lip 50 extends from the end of the peripheral wall 18 of the distal portion 16 that is remote to the end wall 19 of the distal portion 16. The second lip 50 comprises a distal-facing surface 50A.

When the proximal portion 17 of the housing 11 is in the initial position (as shown in FIG. 1), the proximal-facing surface 49A of the first lip 49 abuts the distal-facing surface 50A of the second lip 50 to limit the range of axial movement between the proximal portion 17 and the distal portion 16 such that the proximal portion 17 is prevented from moving away from the distal portion 16 and being separated therefrom.

The third stop 51 is in the form of a recess 51 that extends into the outer surface of the peripheral wall 18 of the distal portion 16. A distal-facing surface 51A is formed at the edge of the recess 51.

The latch 48 further comprises an angled surface 52 that extends between the distal-facing surface 50A of the second stop 50 and the distal-facing surface 51A of the third stop 51. The angled surface 52 is angled slightly with respect to the central axis A-A of the housing 11 such that the angled surface 52 extends slightly away from the central axis A-A of the housing in the direction from the second stop 50 to the third stop 51. The angled surface 52 is formed from a portion of the outer surface of the peripheral wall 18 of the distal portion 16.

The angled surface 52 is configured such that when the proximal portion 17 is moved from the initial position to the primed position the first lip 49 moves over the angled surface 52 and is urged radially outwardly by the angled surface 52 such that the first lip 49 is urged away from the central axis A-A of the housing 11. The thickness and material of the proximal portion 17 is such that when the first lip 49 moves over the angled surface 52 the peripheral wall 20 of the proximal portion 17 resiliently deforms radially outwardly. This flexing of the peripheral wall 20 facilitates movement of the first lip 49 over the angled surface 52. Similarly, the distal portion 16 may also have a thickness and/or be manufactured from a material that allows for the peripheral wall 18 of the distal portion 16 to flex radially inwardly as the first lip 49 moves over the angled surface 52. The distal and proximal portions 16, 17 may be manufactured from, for example, plastic or metal.

Movement of the proximal portion 17 from the initial positon to the primed position causes the first lip 49 to move over the angled surface 52 from the second lip 50 towards the recess 51. When the first lip 49 reaches the recess 51, the first lip 49 moves radially inwardly to 'snap' into the recess 51 such that the proximal-facing surface 49A of the first lip 49 abuts the distal-facing surface 51A at the edge of the recess 51. Thus, the proximal portion 17 is held in place in the primed position such that the end wall 21 of the proximal portion 17 is resisted from moving away from the end wall 19 of the distal portion 16.

The angled surface 52 is arranged to provide a small amount of resistance to the first lip 49 moving over the angled surface 52 from the second lip 50 towards the recess 51, due to the first lip 49 being urged radially outwardly when the proximal portion 17 is moved towards the primed position. Therefore, the patient must overcome a small amount of resistance to move the proximal portion 17 relative to the distal portion 16 from the initial position to the primed position. This reduces the likelihood of the proximal portion 17 being accidentally moved to the primed position.

An exemplary operation of the medicament delivery device 10 will now be described. The medicament delivery device 10 is typically stored in a sterile packaging (not shown). The patient first removes the medicament delivery device 10 from the sterile packaging. When the medicament delivery device 10 is removed from the sterile packaging the proximal portion 17 of the housing 11 is in the initial position, the needle 12 is in the retracted position, and the button 15 is retracted into the proximal portion 17 (as shown in FIG. 1) such that the patient is not able to access the button 15 to actuate the button 15. For example, the inner dimension of the internal wall 17A of the proximal portion 17 may be sufficiently small that the patient is not able to insert a finger into the internal wall 17A to access the button 15. Thus, the patient is not able to depress the button 15 to operate the dispensing mechanism 14 to dispense medicament from the flexible bag 23 and thus the dispensing mechanism 14 is rendered inoperable. Moreover, the patient is not able to operate the needle actuating mechanism 13 to move the needle 12 to the extended position.

The patient then supplies medicament to the dispensing mechanism 14 of the medicament delivery device 10. More specifically, the patient supplies medicament to the flexible bag 23 via the filling port 18A in the peripheral wall 18 of the distal portion 16 of the housing 11. The medicament may be supplied from, for example, a syringe, container, or pressurised canister. In an alternative embodiment, the medicament reservoir 23 is pre-filled with medicament, in which case the filling port 18A may be omitted.

The label (not shown) is then removed from the adhesive layer (not shown) on the outer surface 19A of the end wall 19 of the distal portion 16. The adhesive layer is then adhered to the patient's skin at the injection site such that the end wall 19 of the distal portion 16 is secured to the injection site.

The patient then applies a force to the proximal portion 17 of the housing 11 to move the proximal portion 17 from the initial position to the primed position. For example, the patient may use one hand to apply a force to the outer surface 21A of the distal wall 21 of the proximal portion 17 to push said distal wall 21 towards the distal wall 19 of the distal portion 16. As the proximal portion 17 is moved towards the primed position, the dispensing spring 25 is compressed between the inner surface 21B of the distal wall 21 of the proximal portion 17 and the proximal facing surface 24B of the plate 24 such that a biasing force is exerted on the plate 24 that urges the plate 24 towards the end wall 19 of the distal portion 16. However, the dispensing locking members 27 are initially in the locked state to hold the plate 24 in position against the force of the dispensing spring 25.

When the proximal portion 17 reaches the primed position, the first stop 49 engages with the third stop 51 such that the proximal portion 17 is retained in the primed position. The dispensing spring 25, which is compressed, urges the distal wall 21 of the proximal portion 17 away from the plate 24 when the proximal portion 17 is in the primed position such that the proximal portion 17 is biased away from the primed position by the force of the dispensing spring 25. However, the engagement between the first and third stops 49, 51 is such to prevent the proximal portion 17 from moving away from the primed position under the force of the dispensing spring 25. Therefore, once the patient has moved the proximal portion 17 to the primed position the patient no longer needs to apply a force to the end wall 21 of the proximal portion 17 to retain the proximal portion 17 in the primed position.

Figure 2:
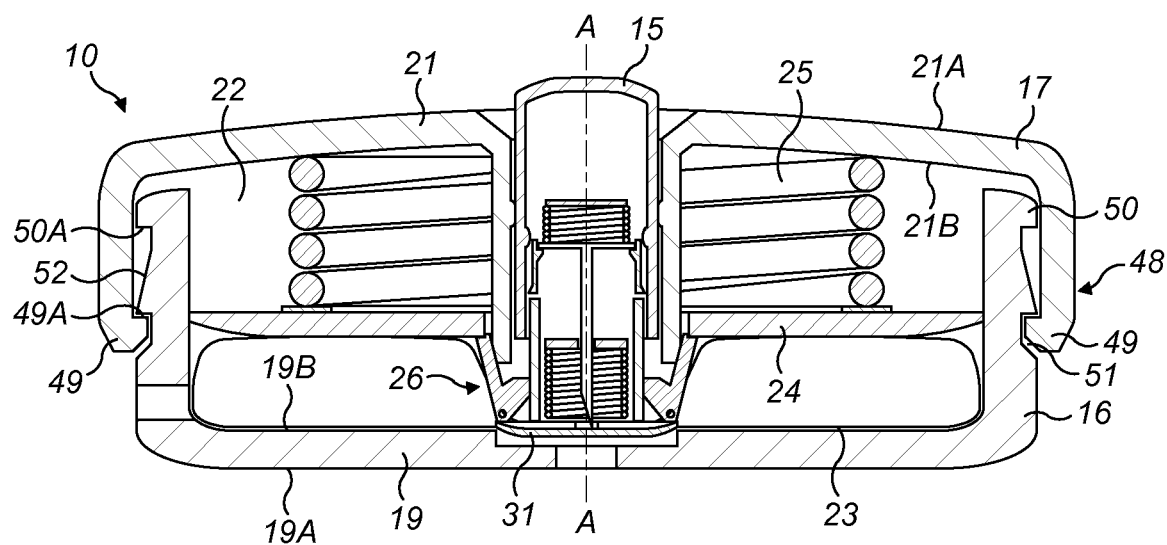
FIG. 2 is a schematic cross-sectional side view of the medicament delivery device of FIG. 1, wherein the proximal portion is in a primed position and a button projects from the proximal portion.
Figure 3:
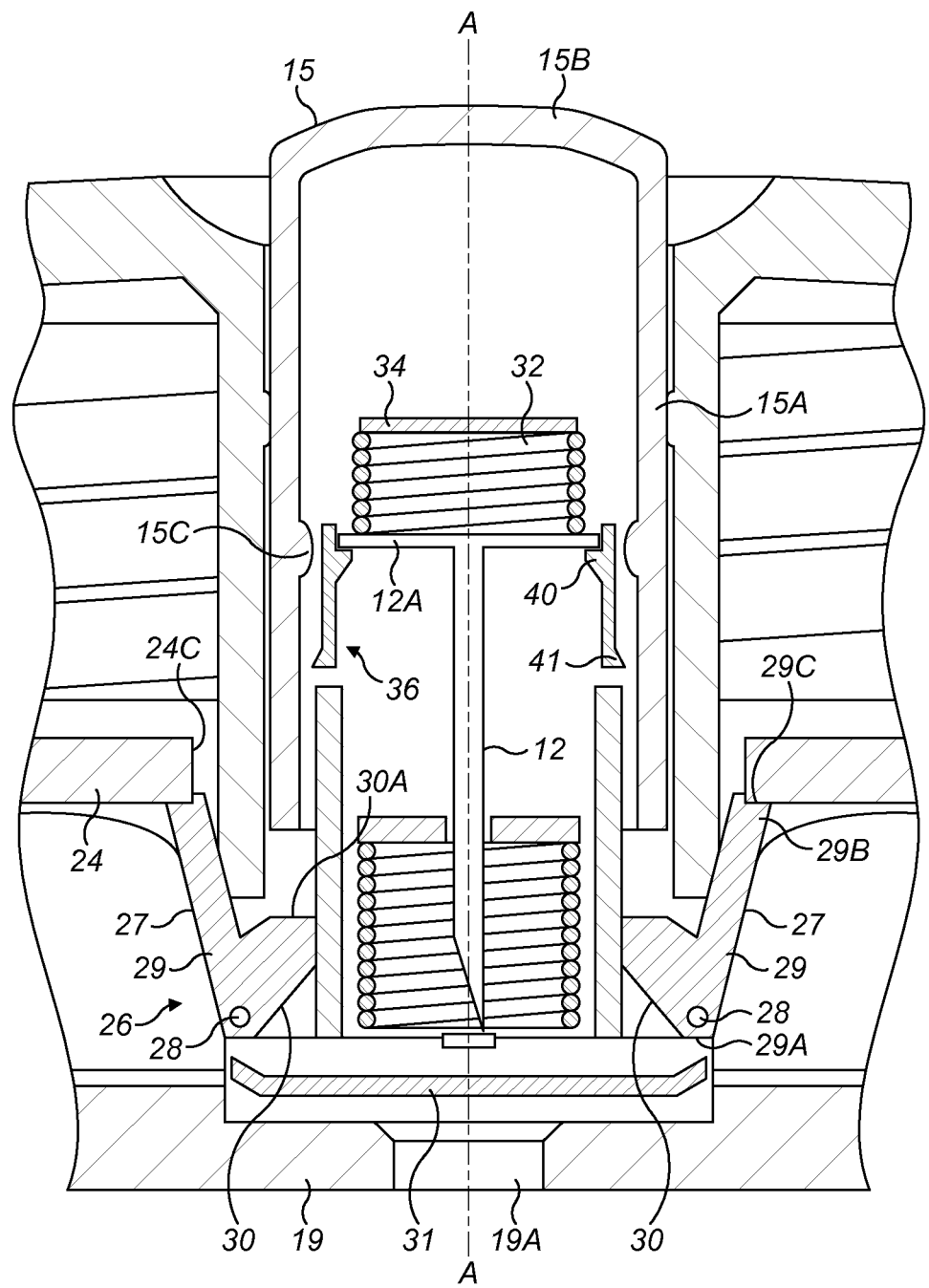
FIG. 3 is a close-up schematic cross-sectional side view of part of the medicament delivery device of FIG. 1.

The button 15 is received in the internal wall 17A of the proximal portion 17 of the housing 11 such that when the proximal portion 17 is moved to the primed position the proximal portion 17 slides relative to the button 15. This causes the button 15 to project from the proximal portion 17 (as shown in FIG. 2). Therefore, the button 15 may be actuated by the patient. The button 15 projects from the end wall 21 of the proximal portion 17 when the proximal portion 17 is in the primed position.

With the proximal portion 17 in the primed position, the medicament delivery device 10 is primed for supplying medicament to the injection site of the patient. The patient depresses the end wall 15B of the button 15 such that the button 15 is slid into the proximal portion 17 of the housing 11. This causes the button 15 to engage with the needle extension lock 36 such that the needle extension spring 32 is released to move the needle 12 to the extended position. In more detail, the button 15 is slid towards the end wall 19 of the distal portion 16 until the projection 15C of the button 15 is urged against the angled surface 41A of the second projection 41 of each extension locking member 38, resulting in each extension locking member 38 rotating from the locked state (shown in FIG. 3) to the unlocked state (shown in FIG. 5). As discussed above, this allows the base 12A of the needle 12 to move away from the extension holding element 34 under the force of the needle extension spring 32 such that the needle 12 moves axially to pass through the septum 31 to extend out of the aperture 19C in the end wall 19 of the distal portion 16. Thus, the needle 12 is moved to the extended position (as shown in FIG. 7). The end wall 19 of the distal portion 16 is adhered to the patient's skin and therefore when the needle 12 is moved to the extended position the needle 12 enters the injection site of the patient.

When the needle 12 is moved to the extended position the needle 12 is fluidly communicated with the inside of the flexible bag 23. In one embodiment, a conduit (not shown) is provided that is fluidly connected to the inside of the flexible bag 23. The needle 12 comprises an aperture (not shown) that aligns with the conduit to fluidly communicate therewith when the needle 12 is moved to the extended position such that medicament is able to flow out of the flexible bag 23, through the conduit, and into the aperture of the needle 12 to be dispensed from the needle 12.

The patient continues to push the button 15 into the housing 11 to then engage the button 15 with the dispensing lock 26 such that, after the needle 12 has been moved to the extended position, the dispensing spring 25 is released to urge the plate 24 towards the end wall 19 of the distal portion 16 such that medicament is dispensed from the flexible bag 23. More specifically, the distal end of the button 15 is urged against the free end 30A of the projection 30 of each dispensing locking member 27, resulting in each dispensing locking member 27 rotating from the locked state (shown in FIG. 3) to the unlocked state (shown in FIG. 6). As discussed above, this allows the plate 24 to move towards the end wall 19 of the distal portion 16 under the force of the dispensing spring 25. Therefore, the flexible bag 23 is compressed between the plate 24 and the end wall 19 of the distal portion 16 such that the pressure of the medicament in the flexible bag 23 is increased and therefore the medicament flows out of the flexible bag 23 and flows through the needle 12 to enter the injection site of the patient.

Once the button 15 has been depressed to the extent that the dispensing locking members 27 are moved to the unlocked state to commence medicament delivery, the patient may stop pressing the button 15. The plate 24 will continue to move towards the end wall 19 of the distal portion 16 such that the flexible bag 23 is compressed and thus medicament is delivered to the injection site of the patient via the needle 12. Therefore, the medicament delivery device 10 may be used to deliver medicament to the injection site of the patient over an extended time period, for example, several hours, without requiring the patient to continuously apply a force to the button 15.

Medicament will continue to be delivered to the injection site until the plate 24 moves to a position within the housing 11 wherein the plate 24 engages with the needle retraction lock 37 such that the needle retraction spring 33 is released to move the needle 12 to the retracted position. In more detail, the plate 24 is moved towards the end wall 19 of the distal portion 16 under the force of the dispensing spring 25 until the plate 24 is urged against the free end 44A of each first elongate member 44 of the retraction locking members 42, resulting in each retraction locking member 42 rotating from the locked state (shown in FIG. 9A) to the unlocked state (shown in FIG. 9B). As discussed above, this allows the retraction holding element 35 to move away from the end wall 19 of the distal portion 16 under the force of the needle retraction spring 33 such that the retraction holding element 35 is urged against the base 12A of the needle 12 to move the needle 12 into the housing 11 to the retracted position (as shown in FIGS. 8 and 9B). The patient may then remove the medicament delivery device 10 from the injection site.

In one embodiment (not shown), a lock may be provided to lock the button 15 in position when the proximal portion 17 is in the initial positon. The lock may comprise a locking member that is in a locked state when the proximal portion 17 is in the initial position to prevent movement of the button 15 relative to the housing 11. The locking member is moved to an unlocked state when the proximal portion 17 is moved to the primed position such that the button 15 can be moved relative to the housing 11.

In the above described embodiment the needle extension and retraction springs 32, 33 are pre-compressed such that the springs 32, 33 are in a compressed state prior to the proximal portion 17 of the housing 11 being moved to the primed position. However, in an alternative embodiment (not shown), the needle extension and retraction springs 32, 33 are in a substantially uncompressed state when the proximal portion 17 is in the initial position and movement of the proximal portion 17 to the primed position compresses the extension and retraction springs 32, 33. For example, the extension holding element 34 may instead be fixed relative to the proximal portion 17 such that movement of the proximal portion 17 from the initial position to the primed position moves the extension holding element 34 towards the end wall 19 of the distal portion 16. Thus, the needle extension spring 32 is compressed between the extension holding element 34 and the base 12A of the needle 12.

Although in the above described embodiment the proximal portion 17 is moved from the initial position to the primed position to compress the dispensing spring 25, in an alternative embodiment (not shown) the dispensing spring 25 is pre-compressed such that the dispensing spring 25 is held in a compressed state when the proximal portion 17 is in the initial position.

In the above described embodiment the actuator 15 is fully received within the housing 11 when the proximal portion 17 is in the initial position. However, in an alternative embodiment, the actuator 15 is configured to project from the proximal portion 17 of the housing 11 when the proximal portion 17 is in the initial and primed positions. In one such embodiment, the actuator 15 is of sufficient length to project from the end wall 21 of the proximal portion 17 when the proximal portion 17 is in the initial position.

In the above described embodiment, the dispensing biasing member 25 and the needle extension and retraction biasing members 32, 33 comprise respective springs 25 32, 33. However, in alternative embodiments (not shown) one or more of the dispensing biasing member 25, the needle extension biasing member 32 and the needle retraction biasing member 33 comprise a different type of biasing member, for example, a portion of resiliently deformable material that is compressed to exert a biasing force.

In the above described embodiment, the medicament delivery device 10 comprises a latch 48 that allows for the proximal portion 17 to be moved relative to the distal portion 16. However, in an alternative embodiment (not shown) the latch is omitted and instead the distal and proximal portions 16, 17 comprise respective screw threads. The screw threads engage such that the proximal portion 17 of the housing 11 can be screwed to the distal portion 16 such that the end wall 21 of the proximal portion 17 moves towards the end wall 19 of the distal portion 16. In one such embodiment, a first screw thread is provided on the outer surface of the peripheral wall 18 of the distal portion 16 and a second screw thread is provided on the inner surface of the peripheral wall 20 of the proximal portion 17. In another embodiment, the distal and proximal portions 16, 17 of the housing 11 are fixed relative to each other, and may be integrally formed.

In the above described embodiment, the medicament delivery device 10 comprises a pair of dispensing locking members 27, a pair of extension locking members 38, and a pair of retraction locking members 42. However, in alternate embodiments (not shown), the medicament delivery device 10 instead comprises a single dispensing locking member 27, a single extension locking member 38 and/or a single retraction locking member 42.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta-decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The invention claimed is:

1. A medicament delivery device comprising:
   a housing;
   a needle moveable from a retracted position, in which the needle is fully received in the housing, to an extended position, in which the needle protrudes out of the housing;
   a medicament delivery mechanism comprising a reservoir and a dispensing member each disposed in the housing, first and second biasing members, and first and second locking members; and
   an actuator moveable relative to the housing from an initial position to an intermediate position such that the actuator exerts a force on the first locking member to urge the first locking member from a locked state to an unlocked state in which the first biasing member moves the needle from the retracted position to the extended position,
   wherein the actuator is moveable into the housing from the intermediate position to a second position such that the actuator exerts a force on the second locking member to urge the second locking member from a locked state to an unlocked state in which the second biasing member moves the dispensing member within the housing to dispense medicament from the reservoir when the reservoir contains the medicament.

2. The medicament delivery device according to claim 1, wherein the actuator comprises a push button that is slidable relative to the housing.

3. The medicament delivery device according to claim 1, wherein the first and/or second locking member is pivotally coupled to the housing.

4. The medicament delivery device according to claim 1, wherein the first locking member comprises a projection, and the actuator is configured to abut the projection when the actuator is moved from the initial position to the intermediate position to move the first locking member to the unlocked state.

5. The medicament delivery device according to claim 4, wherein the first locking member comprises a surface configured to resist movement of the needle to the extended position when the first locking member is in the locked state, wherein the first locking member is pivotally coupled to the housing at a point between the surface and the projection.

6. The medicament delivery device according to claim 1, wherein the second locking member comprises a first portion and a second portion extending at an angle to the first portion, wherein the first portion of the second locking member is configured to abut the dispensing member when the second locking member is in the locked state.

7. The medicament delivery device according to claim 6, wherein the first portion comprises a recess configured to receive at least part of the dispensing member when the second locking member is in the locked state.

8. The medicament delivery device according to claim 6, wherein the actuator is configured to abut the second portion of the second locking member when the actuator is moved from the intermediate position to the second position to move the second locking member to the unlocked state.

9. The medicament delivery device according to claim 1, wherein the medicament delivery mechanism further comprises a third biasing member and a third locking member, wherein the third locking member is moveable from a locked state to an unlocked state wherein the third biasing member moves the needle to the retracted position.

10. The medicament delivery device according to claim 9, wherein the second biasing member is configured to urge the dispensing member against the third locking member such that the third locking member is moved to the unlocked state.

11. The medicament delivery device according to claim 10, wherein the third locking member is pivotally coupled to the housing and comprises a first portion and a second portion extending at an angle to the first portion, wherein the second biasing member is configured to urge the dispensing member against the first portion of the third locking member.

12. The medicament delivery device according to claim 11, wherein the second portion of the third locking member comprises a projection configured to retain the third biasing member in a compressed state when the third locking member is in the locked state.

13. The medicament delivery device according to claim 1, wherein the housing comprises a distal end wall with an adhesive layer.

14. The medicament delivery device according to claim 1, wherein the first locking member is configured to prevent the first biasing member from moving the needle from the retracted position to the extended position when the first locking member is in the locked state.

15. The medicament delivery device according to claim 1, wherein the second locking member is configured to prevent the second biasing member from moving the dispensing member within the housing when the second locking member is in the locked state.

16. The medicament delivery device according to claim 1, wherein the housing comprises first and second portions that are moveable relative to each other from an initial position to a primed position.

17. The medicament delivery device according to claim 16, wherein the first and second portions of the housing are moveable relative to each other from the initial position to the primed position to prime the first biasing member.

18. The medicament delivery device according to claim 16, wherein the first and second portions of the housing are moveable relative to each other from the initial position to the primed position to prime the second biasing member.

19. The medicament delivery device according to claim 1, wherein the reservoir contains the medicament.

20. The medicament delivery device according to claim 1, wherein the housing comprises distal and proximal ends, wherein in the extended position the needle protrudes out of the distal end of the housing, and wherein the proximal end is opposite to the distal end, and wherein the actuator is located at the proximal end.

21. The medicament delivery device according to claim 1, wherein the second locking member is configured to prevent the dispensing member from moving within the housing when the second locking member is in the locked state.

22. The medicament delivery device according to claim 1, wherein the dispensing member is configured to remain stationary relative to the reservoir when the first locking member is urged from the locked state to the unlocked state in which the first biasing member moves the needle from the retracted position to the extended position.

23. The medicament delivery device according to claim 1, wherein the dispensing member comprises opposite first and second sides, wherein the second biasing member is located on the first side of the dispensing member and the reservoir is located on the second side of the dispensing member.

24. The medicament delivery device according to claim 1, wherein the reservoir comprises a flexible bag.

25. A medicament delivery mechanism for a medicament delivery device, the medicament delivery mechanism comprising:
 a reservoir configured to contain medicament and configured to be disposed in a housing of the medicament delivery device;
 a dispensing member configured to dispense the medicament from the reservoir and configured to be disposed in the housing of the medicament delivery device;
 first and second biasing members;
 a first locking member configured to lock the first biasing member in a locked state, wherein the first locking member is configured to be urged by an actuator of the medicament delivery device moveable into the housing of the medicament delivery device from the locked state to an unlocked state in which the first biasing member extends a needle of the medicament delivery device from the medicament delivery device;
 a second locking member configured to lock the second biasing member in a locked state, wherein the second locking member is configured to be urged by the actuator from the locked state to an unlocked state in which the second biasing member moves the dispensing member within the housing of the medicament delivery device to dispense medicament from the reservoir.

26. A method of dispensing medicament from a medicament delivery device, the method comprising:
 moving an actuator of the medicament delivery device relative to a housing of the medicament delivery device from an initial position to an intermediate position such that the actuator exerts a force on a first locking member of a medicament delivery mechanism of the medicament delivery device to urge the first locking member of the medicament delivery mechanism from a locked state to an unlocked state, in which a first biasing member of the medicament delivery mechanism moves a needle of the medicament delivery device from a retracted position in which the needle is fully received in the housing, to an extended position, in which the needle protrudes out of the housing; and
 moving the actuator into the housing from the intermediate position to a second position such that the actuator exerts a force on a second locking member of the medicament delivery mechanism to urge the second locking member of the medicament delivery mechanism from a locked state to an unlocked state in which a second biasing member of the medicament delivery mechanism moves a dispensing member of the medicament delivery mechanism within the housing to dispense the medicament from a reservoir of the medicament delivery mechanism.

\* \* \* \* \*